(12) United States Patent
Kim et al.

(10) Patent No.: US 12,427,186 B2
(45) Date of Patent: Sep. 30, 2025

(54) METHOD FOR TREATING GROWTH HORMONE DEFICIENCY EMPLOYING hGH FUSION PROTEIN

(71) Applicants: GENEXINE, INC., Seongnam-si (KR); HANDOK INC., Seoul (KR)

(72) Inventors: Tae Kyung Kim, Seongnam-si (KR); Jung Won Woo, Seoul (KR); Joan Yoon Ji Lee, Seongnam-si (KR); Young-Joo Ahn, Seongnam-si (KR); Ji-Eun Cha, Seongnam-si (KR); Hyou Young Rhim, Gwacheon-si (KR); Woo Ick Jang, Seoul (KR)

(73) Assignees: GENEXINE, INC., Seongnam-si (KR); HANDOK INC., Seoul (KR)

( * ) Notice: Subject to any disclaimer, the term of this patent is extended or adjusted under 35 U.S.C. 154(b) by 375 days.

(21) Appl. No.: 16/329,317

(22) PCT Filed: Aug. 30, 2017

(86) PCT No.: PCT/KR2017/009471
§ 371 (c)(1),
(2) Date: Feb. 28, 2019

(87) PCT Pub. No.: WO2018/044060
PCT Pub. Date: Mar. 8, 2018

(65) Prior Publication Data
US 2019/0224281 A1 Jul. 25, 2019

(30) Foreign Application Priority Data

Aug. 30, 2016 (KR) .................. 10-2016-0110806
Aug. 30, 2017 (KR) .................. 10-2017-0110161

(51) Int. Cl.
*A61K 38/27* (2006.01)
*A61K 9/00* (2006.01)
*A61P 5/06* (2006.01)
*C07K 14/61* (2006.01)
*G01N 33/74* (2006.01)

(52) U.S. Cl.
CPC ............ *A61K 38/27* (2013.01); *A61K 9/0019* (2013.01); *A61P 5/06* (2018.01); *C07K 14/61* (2013.01); *G01N 33/74* (2013.01); *C07K 2319/30* (2013.01); *G01N 2333/61* (2013.01)

(58) Field of Classification Search
None
See application file for complete search history.

(56) References Cited

U.S. PATENT DOCUMENTS

| 7,867,491 | B2 | 1/2011 | Yang et al. |
| 8,529,899 | B2 | 9/2013 | Yang et al. |
| 8,883,134 | B2 | 11/2014 | Cho et al. |
| 2010/0247608 | A1 | 9/2010 | Azria et al. |
| 2010/0261248 | A1 | 10/2010 | Kim et al. |
| 2012/0276097 | A1 | 11/2012 | Yang et al. |
| 2014/0162949 | A1 | 6/2014 | Cleland et al. |
| 2014/0162954 | A1 | 6/2014 | Brown et al. |
| 2016/0108105 | A1 | 4/2016 | Yang et al. |
| 2021/0177945 | A1 | 6/2021 | Kim et al. |

FOREIGN PATENT DOCUMENTS

| CN | 105209055 A | 12/2015 |
| JP | 2016-508125 A | 3/2016 |
| JP | 2016-514132 A | 5/2016 |
| WO | 2015/059695 A1 | 4/2015 |
| WO | 2016/011281 A1 | 1/2016 |
| WO | 2016/079302 A1 | 5/2016 |
| WO | 2017/142331 A1 | 8/2017 |

OTHER PUBLICATIONS https://pipelinereview.com/index.php/2013082051798/Proteins-and-Peptides/Handok-Genexine, 2013.*
Cleland et al. (J Pharm Sci 101: 2744-2754, 2012).*
Drake et al. J. Clin. Endocrinol. Metab. 83: 3913-3919, 1998).*
Kim et al. (Mol. Pharmaceutics 12: 3759-3765, 2015).*
Strohl et al. (BioDrugs 29: 215-239, 2015).*
PipelineReview.com, Proteins and Peptides, "Handok-Genexine Long-Acting hGH Therapeutic "GX-HO" Receives Approval for Phase I Trial in Europe", 2013.*
Charlotte Hoybye et al., "Status of long-acting-growth hormone preparations", Growth Hormone & IGF Research, 2015, pp. 201-206, vol. 25.
Jung-Won Woo et al., "A Hybrid Fc-Fused Human Growth Hormone, GX-H9, Shows a Potential for Semi-Monthly Administration in Clinical Studies", Endocrine Society's 98th Annual Meeting and Expo, May 3, 2016, 4 pages.
Eung-Sam Kim et al., "Controlled release of human growth hormone fused with a human hybrid Fc fragment through a nanoporous polymer membrane", Nanoscale, 2013, pp. 4262-4269, vol. 5.
David M. Cook et al., "Guidelines for Use of Growth Hormone in Clinical Practice", Endocrine Practice, 2009, vol. 15(Suppl 2), pp. 1-29 (29 pages total).
Wayne S. Cutfield et al., "Non-Compliance with Growth Hormone Treatment in Children Is Common and Impairs Linear Growth", PLos One, 2011, vol. 6, Issue 1, pp. 1-3 (3 pages total).

(Continued)

*Primary Examiner* — Christine J Saoud
(74) *Attorney, Agent, or Firm* — Sughrue Mion, PLLC

(57) ABSTRACT

A method for treating growth hormone deficiency, including administering a human growth hormone fusion protein (GX-H9). A method includes administering a pharmaceutical composition containing an hGH fusion protein (GX-H9) and a pharmaceutically acceptable carrier, wherein the fusion protein (GX-H9) is administered once a week at a dose of 0.4 to 1.6 mg per body weight kg of a pediatric patient, or administered once every two weeks at a dose of 0.8 to 3.2 mg per body weight kg of a pediatric patient.

7 Claims, 10 Drawing Sheets
Specification includes a Sequence Listing.

(56) References Cited

OTHER PUBLICATIONS

GH Research Society, "Consensus Guidelines for the Diagnosis and Treatment of Growth Hormone (GH) Deficiency in Childhood and Adolescence: Summary Statement of the GH Research Society", Journal of Clinical Endocrinology & Metabolism, 2000, vol. 85, No. 11, pp. 3990-3993 (4 pages total).
Ron G. Rosenfeld et al., "Compliance and Persistence in Pediatric and Adult Patients Receiving Growth Hormone Therapy", Endocrine Practice, 2008, vol. 14, No. 2, pp. 143-154 (12 pages total).
"Handok-Genexine Long-Acting hGH Therapeutic "GX-H9" Receives Approval for Phase I Trial in Europe", Aug. 20, 2013, retrieved Jul. 6, 2019, https://pipelinereview.com/index.php/2013082051798/Proteins-and-Peptides/Handok-Genexine-Long-Acting-hGH-Therapeutic-GX-H9-Receives-Approval-for-Phase-I-Trial-in-Europe.html, (2 pages).
"New therapeutic products for chronic hepatitis C patient", Journal of Clinical and Experimental Medicine, 2008, vol. 225, No. 4, pp. 348-349 (6 pages total).
Anonymous, "New Government Initiative for Drug Development—Korea Drug Development", Jan. 1, 2013, pp. 1-20, XP05562192 (20 pages total).
Eungjig Lee et al., "A Hybrid Fc-fused Human Growth Hormone, GX-H9, Shows a Potential for Weekly and Semi-monthly Administration in Clinical Studies", 55th Annual ESPE, 2016, XP055622148, pp. 1-3 (3 pages total).
Anonymous, "KDDF-201308-07 Conduct and Completion of a Global Clinical Phase I Trial of a Next-Generation Human Growth Hormone Product(Metabolic Disorders,)", Korea Drug Development Fund, 2016, XP055622221, pp. 1-2 (2 pages total).
Anonymous, "Development and Technology Transfer of Recombinant Human Growth Hormone Deficiency Therapeutics using Long-Acting Fc Fusion Protein Platform", Korea Drug Development Fund, 2016, XP055622234, pp. 1-3 (3 pages total).
Anonymous, "EU Clinical Trials Register", Clinical Trials Register, EudraCT No. 2015-001939-21, 2015, XP055622245, pp. 1-6 (6 pages total).
Anonymous, "EU Clinical Trials Register", EudraCT No. 2014-002698-13, 2014, XP055622300, pp. 1-5 (5 pages total).
International Search Report dated May 17, 2017 in International Application No. PCT/KR2017/001726.
Written Opinion of the International Searching Authority dated May 17, 2017 in International Application No. PCT/KR2017/001726.
Cheol Ryong Ku et al., "Long-acting FC-fusion rhGH (GX-H9) shows potential for up to twice- monthly administration in GH-deficient adults", European Journal of Endocrinology, 2018, vol. 179, pp. 168-179 (11 pages total).
Woo, J.-W., et al., "The Endocrine Society's 98th Annual Meeting and Expo, Apr. 1-4, 2016—Boston", Endocrine Reviews, vol. 37, Issue Supplement, Apr. 1, 2016, pp. 2-4 (4 pages total).
Communication dated Apr. 11, 2023 issued by the Japanese Patent Office in JP application No. 2019-532910.
MacGillivray et al., "Current Dosing of Growth Hormone in Children With Growth Hormone Deficiency: How Physiologic?", Pediatrics, 1998, 102, Supplement_3, 527-530.

* cited by examiner

Fig. 10
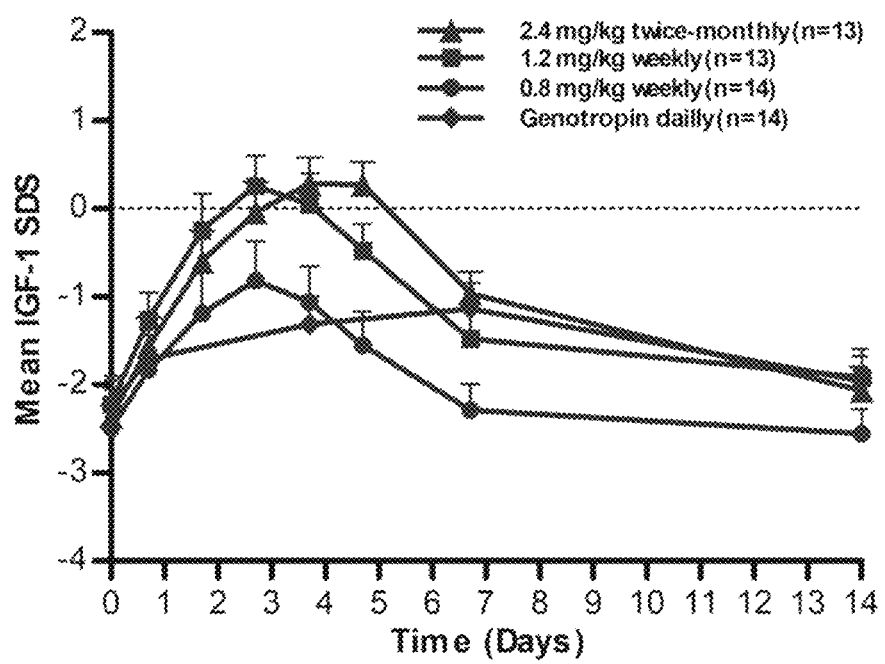
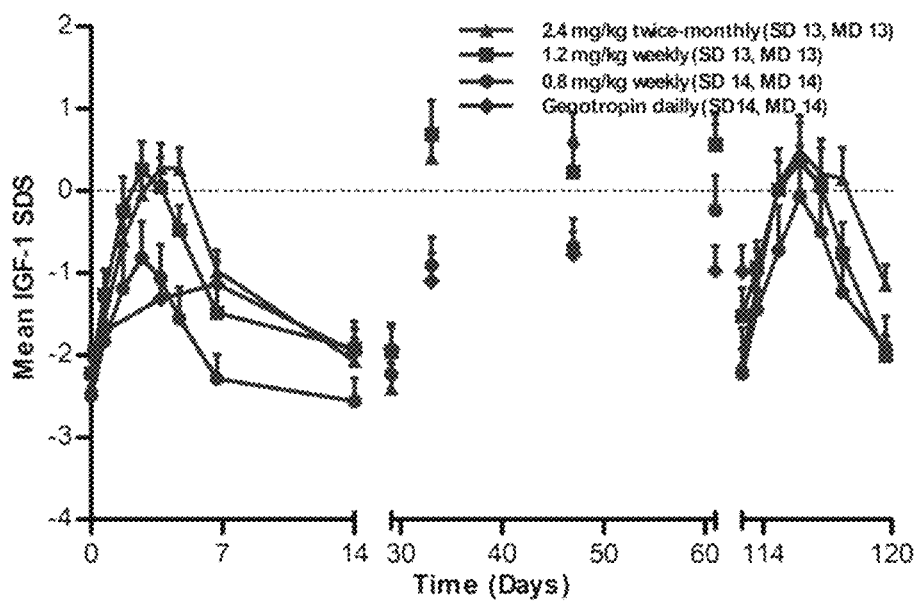

METHOD FOR TREATING GROWTH HORMONE DEFICIENCY EMPLOYING hGH FUSION PROTEIN

CROSS REFERENCE TO RELATED APPLICATIONS

This application is a National Stage of International Application No. PCT/KR2017/009471 filed Aug. 30, 2017, claiming priority based on Korean Patent Application Nos. 10-2016-0110806 filed Aug. 30, 2016 and 10-2017-0110161 filed Aug. 30, 2017.

TECHNICAL FIELD

The present disclosure relates to a pharmaceutical composition for treating growth hormone deficiency, which comprises a human growth hormone fusion protein hGH-hyFc (GX-H9) produced by fusing a hybrid Fc to a human growth hormone (hGH). Specifically, the present disclosure relates to a method for administering the hGH fusion protein effective in treating growth hormone deficiency, and a pharmaceutical composition for treating growth hormone deficiency, which comprises an hGH fusion protein (GX-H9) and a pharmaceutically acceptable carrier, wherein the hGH fusion protein (GX-H9) is administered once a week at a dose of 0.4 to 1.6 mg per body weight kg of a patient, or administered once every two weeks at a dose of 0.8 to 3.2 mg per body weight kg of a patient.

In addition, the present disclosure relates to a method for treating growth hormone deficiency, which comprising a step of administering an hGH fusion protein (GX-H9) to a pediatric patient with growth hormone deficiency once a week at a dose of 0.4 to 1.6 mg per body weight kg of the patient, or once every two weeks at a dose of 0.8 to 3.2 mg per body weight kg of the patient.

Further, the present disclosure relates to a kit comprising: a container comprising an hGH fusion protein and a pharmaceutically acceptable carrier; and an insert indicating that the hGH fusion protein is administered to a patient once a week at a dose of 0.4 to 1.6 mg/kg per body weight kg of the patient or once every two weeks at a dose of 0.8 to 3.2 mg per body weight kg of the patient in order to treat growth hormone deficiency.

BACKGROUND ART

Growth hormone, a single-molecule polypeptide consisting of 191 amino acids, is a hormone that is secreted from the anterior pituitary gland. Growth hormone binds to growth hormone receptor to express IGF-1 (Insulin like Growth Factor-1) which is involved in the growth and regeneration of cells. It is known that growth hormone is synthesized in the pituitary gland in the body of normal persons, and the production thereof increases up to puberty and decreases gradually with age.

Typical growth hormone deficiency disorders include adult growth hormone deficiency (AGHD) and pediatric growth hormone deficiency (PGHD). Adult growth hormone deficiency occurs when the patient's pituitary gland is damaged by radiation or surgery during treatment of brain tumors, cerebral hemorrhage, etc., or occurs idiopathically. If secretion of growth hormone is not normal, symptoms, including body weight loss, decreased bone mineral density, increased fat, decreased HDL, increased LDL, decreased muscle strength, and the like, occur to reduce the quality of life. Patients with adult growth hormone deficiency have an IGF-1 standard deviation score (SDS) of −2 or less (<−2 SDS) or <$2.5^{th}$ percentile of normal for age. Blood growth hormone levels can be measured by stimulation tests, including insulin tolerance test (ITT), GHRH+arginine stimulation test (GHRH+ARG), glucagon test, L-DOPA test, clonidine tests and the like. If the peak growth hormone (GH) level is 11.0 μg/L or lower in patients with a body mass index (BMI) of less than 25 kg/m², 8.0 μg/L or lower in patients with a body mass index of 25 to 30 kg/m², or 4.0 μg/L or lower in patients with a body mass index of more than 30 kg/m², these patients are determined to have growth hormone deficiency (Guidelines for Use of Growth Hormone in Clinical Practice, *Endocr. Pract.* 2009; 15 (Suppl 2)).

Pediatric growth hormone deficiency occurs when there is damage to the pituitary gland or developmental disability. If growth hormone secretion is impaired, short stature appears, in which growth corresponding to the lower 3% in a growth curve of the same age group or to 5 cm or less per year appears, and symptoms also appear, including low glucose levels, decreased physical fitness, depression and mental immaturity. The following children may be determined to have pediatric growth hormone deficiency: children whose height is at least 3 SD lower than the mean value in the same age group; children whose height is at least 1.5 SD lower than the mean height of parents; children who are at least 2 SD lower than the mean value and are at least 1 SD lower than the growth of the same age group for a period of 1 year or more; children 2 years or older, but have an SD value of at least 0.5 lower; or children who show no short stature symptoms, but have an SD of less than 2 for 1 year or more or maintain an SD of 1.5 for 2 years or more (Consensus guideline for the diagnosis and treatment of GH deficiency in childhood and adolescence: summary statement of the GH Research Society. GH Research Society, *J. Clin. Endocrinol. Metab.*, 2000 November; 85(11): 3990-3).

For adult growth hormone deficiency, the dose of a drug was determined based on the patient's body weight in conventional arts, but in recent years, a dose individualized for each patient has been used for treatment. Specifically, after treatment starts with a dose lower than an estimated appropriate dose, the dose is increased or decreased in the range of 0.1 to 0.2 mg/day depending on clinical responses, adverse event cases, or IGF-1 levels. The therapeutic dose of growth hormone should be determined considering the sex, estrogen level, age and the like of the patient. Treatment of adult growth hormone deficiency aims to normalize metabolism and improve the quality of life. To this end, the dose of growth hormone should be suitably determined such that blood IGF-1 levels will be in a normal range (from −2 SDS to 2 SDS) depending on the age and sex of the patient.

For pediatric growth hormone deficiency, it is recommended to start treatment as soon as possible after being diagnosed of having pediatric growth hormone deficiency. Generally, a regime of subcutaneously administering growth hormone in the evening everyday is used, and the recommended dose of growth hormone is 25 to 50 μg/kg/day. Generally, it is recommended to check the rate of growth at 3-month or 6-month intervals, monitor height growth, a change in growth rate, individual patient's compliance, check adverse events for confirming safety, and measure serum IGF-1 or IGFBP-3 levels. Treatment of pediatric growth hormone deficiency patients aims to normally grow height, and the dose of growth hormone should be suitably determined such that blood IGF-1 levels can be maintained in a normal range (from −2 SDS to 2 SDS) depending on the age and sex of the patient.

When growth hormone treatment was first introduced in 1950s, growth hormones were extracted from dead human bodies, and the amount of growth hormones obtainable from one person was very limited, and for this reason, the growth hormones were difficult to supply steadily and were also costly. Since then, as gene recombination technologies have been developed, growth hormones synthesized in E. coli have been marketed (Somatropin, 1981, Genentech, USA). Examples of a recombinant growth hormone therapeutic agent currently put on the US market include Genotropin from Pfizer, Humatrope from Eli Lilly, Nutropin from Genentech, Norditropin from Novo Nordisk, etc.

However, the recombinant growth hormone preparations are all once-daily dose forms that need to be administered six times or seven times a week. For adult growth hormone deficiency, Humatrope is used at a dose of 0.2 mg/day (in the range of 0.15 to 0.30 mg/day). When determination of the dose of Nutropin is not based on body weight, the start dose of Nutropin is 0.2 mg/day (in the range of 0.15 to 0.3 mg/day), and the dose may be changed in the range of 0.1 to 0.2 mg/day at intervals of 1 to 2 months. When the dose of Nutropin is determined based on body weight, the start dose thereof is used not more than 0.005 mg/kg/day. When there is a case that the dose of Nutropin needs to be increased, the dose is increased such that it is not more than 0.01 mg/kg/day at 4 weeks after administration. When determination of the dose of Norditropin is not based on body weight, the start dose thereof is 0.2 mg/day (in the range of 0.15 to 0.3 mg/day), and the dose of Norditropin may be changed in the range of 0.1 to 0.2 mg/day at 1 to 2-month intervals. When the dose of Norditropin is determined based on body weight, Norditropin is used such that the start dose thereof is not more than 0.004 mg/kg/day. When the dose of Norditropin needs to be increased, it is increased such that it is not more than 0.016 mg/kg/day after 6 weeks. For pediatric growth hormone deficiency, Genotropin is used at a dose of 0.16 to 0.24 mg/kg/week, and Humatrope is used at a dose of 0.026 to 0.043 mg/kg/day. Furthermore, Norditropin is used at a dose of 0.3 mg/kg/week, and Norditropin is used at a dose of 0.024 to 0.034 mg/kg/day.

Current growth hormone preparations are once-daily dose forms, and particularly, have inconvenience in that they should be injected daily over a long treatment period of 3 to 4 years for pediatric patients. Furthermore, it is known that mental stress resulting from injection of these growth hormone preparations reduces the quality of life. Moreover, a compliance problem often arises in that the patient does not unintentionally receive an injection, and this problem is the biggest factor that impairs the therapeutic effect. In addition, it is known that, as the number of years for treatment increases, the number of non-compliances significantly increases (*Endocrine practice*, 2008 March; 14(2): 143-54). It is known that the height growth rate of about ⅔ of patients decreases due to actual non-compliance (low compliance) (*PloS one*, 2011 January; 6(1): e16223).

Because of such problems, there have been steady attempts to develop long-lasting growth hormones using various technologies. However, among products that were successfully developed and marketed, Nutropin Depot developed by Genentech is a once-monthly dose form, but it was withdrawn from the market due to its difficult production. Furthermore, Eutropin Plus/Declage (LG Life Sciences, Ltd.) was developed as a once-weekly dose form using hyaluronic acid (HA), but has a disadvantage over the first generation products in that it should use a syringe with a large needle.

Thus, in view of the patient's compliance that is reduced due to inconvenience resulting from daily dose and other various reasons, there is a need to develop long-lasting growth hormones that are safe and effective while satisfying patient compliance. GX-H9 (hGH-hybrid Fc) is a long-lasting growth hormone preparation. In U.S. Pat. No. 7,867,491, of which content is incorporated herein by reference in its entirety, a hybrid Fc capable of overcoming complement-dependent cytotoxicity and antibody-dependent cellular cytotoxicity, which are the problems of conventional Fc fusion technologies, was produced by combining immunoglobulin IgD and immunoglobulin IgG4. Then, in U.S. Pat. No. 8,529,899, of which content is incorporated herein by reference in its entirety, an hGH fusion protein (hGH-hyFc, GX-H9) capable of replacing conventional once-daily dose type growth hormone preparations was produced by fusing a hybrid Fc to a human growth hormone (hGH). However, the actual in vivo half life of the Fc fusion protein greatly varies depending on the kind of physiologically active component that binds to the Fc, and it also influences the dose of the fusion protein. The dose, dosage frequency and the like of the fusion protein GX-H9 of human growth hormone (hGH) and hyFc, which are effective and safe in treatment of growth hormone deficiency, have not yet been elucidated.

Accordingly, in order to determine the dose and dosage frequency of the hGH fusion protein GX-H9, which can exhibit optimal effects, the present inventors have performed clinical trials on 32 healthy adults (2013-002771-18), 45 patients with adult growth hormone deficiency (2014-002698-13, EudraCT/NCT02946606, ClinicalTrials.gov) and 56 patients with pediatric growth hormone deficiency (2015-001939-21, EudraCT). As a result, the present inventors have determined the dose, dosage frequency, safety and the like of GX-H9, which can maintain IGF-1 SDS values in a normal range over a long period of time while minimizing side effects that can be caused by the growth hormone, thereby completing the present invention.

DISCLOSURE OF INVENTION

Technical Problem

It is an object of the present disclosure to provide a method for treating growth hormone deficiency using an hGH fusion protein GX-H9 effective in treating growth hormone deficiency by elucidating the dose and dosage frequency of the hGH fusion protein GX-H9.

To achieve the above object, the present disclosure provides a pharmaceutical composition for treating growth hormone deficiency, which comprises an hGH fusion protein GX-H9 and a pharmaceutically acceptable carrier, wherein the hGH fusion protein is administered once a week at a dose of 0.4 to 1.6 mg per body weight kg of a pediatric patient.

The present disclosure also provides a pharmaceutical composition for treating growth hormone deficiency, which comprises an hGH fusion protein GX-H9 and a pharmaceutically acceptable carrier, wherein the hGH fusion protein is administered once every two weeks at a dose of 0.8 to 3.2 mg per body weight kg of a pediatric patient.

The present disclosure also provides a kit comprising: a container containing an hGH fusion protein GX-H9 and a pharmaceutically acceptable carrier; and an insert indicating that the hGH fusion protein is administered to a pediatric patient once a week at a dose of 0.4 to 1.6 mg/kg per body weight kg of the patient in order to treat growth hormone deficiency.

The present disclosure also provides a kit comprising: a container containing an hGH fusion protein GX-H9 and a pharmaceutically acceptable carrier; and an insert indicating that the hGH fusion protein is administered to a pediatric patient once every two weeks at a dose of 0.8 to 3.2 mg/kg per body weight kg of the patient in order to treat growth hormone deficiency.

The present disclosure also provides a method for treating growth hormone deficiency, the method comprising a step of administering an hGH fusion protein GX-H9 to a pediatric patient with growth hormone deficiency once a week at a dose of 0.4 to 1.6 mg per body weight kg of the patient. The present disclosure provides use of an hGH fusion protein GX-H9 in the manufacture of a medicament for treating growth hormone deficiency by administering to a pediatric patient with growth hormone deficiency once a week at a dose of 0.4 to 1.6 mg per body weight kg of the patient. The present disclosure provides a composition comprising hGH fusion protein GX-H9 for use in treating growth hormone deficiency by administering to a pediatric patient with growth hormone deficiency once a week at a dose of 0.4 to 1.6 mg per body weight kg of the patient.

The present disclosure also provides a method for treating growth hormone deficiency, the method comprising a step of administering an hGH fusion protein GX-H9 to a pediatric patient with growth hormone deficiency once every two weeks at a dose of 0.8 to 3.2 mg per body weight kg of the patient. The present disclosure provides use of an hGH fusion protein GX-H9 in the manufacture of a medicament for treating growth hormone deficiency by administering to a pediatric patient with growth hormone deficiency once every two weeks at a dose of 0.8 to 3.2 mg per body weight kg of the patient. The present disclosure provides a composition comprising hGH fusion protein GX-H9 for use in treating growth hormone deficiency by administering to a pediatric patient with growth hormone deficiency once every two weeks at a dose of 0.8 to 3.2 mg per body weight kg of the patient.

BRIEF DESCRIPTION OF THE DRAWINGS

FIG. 10 shows the pharmacodynamic (mean IGF-1 SDS) characteristics depending on the dose in single-dose (SD) period and multi-dose (MD) period of an hGH fusion protein (GX-H9) in a phase-2 clinical trial on patients with pediatric growth hormone deficiency.

BEST MODE FOR CARRYING OUT THE INVENTION

Figure 1:
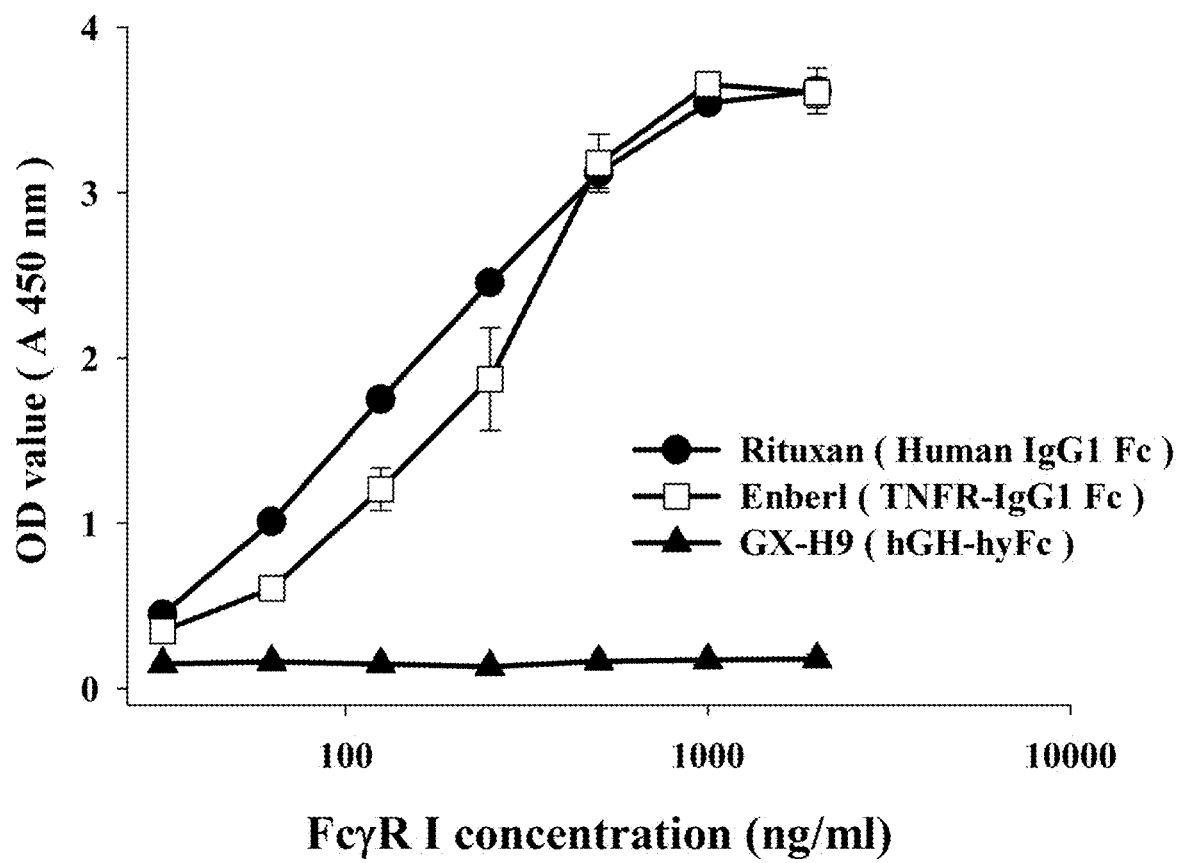
FIG. 1 shows the result of measuring the binding affinity of Fcγ receptor (FcγR) I for an hGH fusion protein (GX-H9).

The dose and dosage frequency of the human growth hormone (hGH) fusion protein GX-H9, which are effective in promoting actual growth in humans, have not yet been elucidated.

The present inventors have performed clinical trials (2015-001939-21) on 56 patients with pediatric hormone deficiency in order to determine the dose and dosage frequency of GX-H9, which can exhibit optimal effects. As a result, the present inventors have found that, when the hGH fusion protein GX-H9 is administered once a week at a dose of 0.4 to 1.6 mg per body weight kg of pediatric patients, or administered once every two weeks at a dose of 0.8 to 3.2 mg per body weight kg of pediatric patients, the growth hormone can be long-lasting in vivo so that the IGF-1 SDS value thereof can be maintained in a normal range for a long period of time.

Therefore, in one aspect, the present disclosure is directed to a pharmaceutical composition for treating growth hormone deficiency, which comprises an hGH fusion protein (GX-H9) and a pharmaceutically acceptable carrier, wherein the hGH fusion protein is administered once a week at a dose of 0.4 to 1.6 mg per body weight kg of a pediatric patient. In particular, the present disclosure is directed to a pharmaceutical composition wherein the hGH fusion protein is administered once a week at a dose of 0.5 to 1.5 mg, 0.7 to 1.3 mg, or 0.8 to 1.2 mg per body weight kg of a pediatric patient.

In addition, in another aspect, the present disclosure is directed to a pharmaceutical composition for treating growth hormone deficiency, which comprises an hGH fusion protein (GX-H9) and a pharmaceutically acceptable carrier, wherein the hGH fusion protein is administered once every two weeks at a dose of 0.8 to 3.2 mg per body weight kg of a pediatric patient. In particular, the present disclosure is directed to a pharmaceutical composition wherein the hGH fusion protein is administered once every two weeks at a dose of 1.0 to 3.0 mg, 1.4 to 2.6 mg, or 1.6 to 2.4 mg per body weight kg of a pediatric patient.

In the pharmaceutical composition of the present disclosure, the hGH fusion protein (GX-H9) may comprise an amino acid sequence of SEQ ID NO: 1. The pharmaceutical composition of the present disclosure may be administered subcutaneously.

In another aspect, the present disclosure is directed to a method for treating growth hormone deficiency, the method comprising a step of administering an hGH fusion protein GX-H9 to a pediatric patient with growth hormone deficiency once a week at a dose of 0.4 to 1.6 mg per body weight kg of the patient.

In still another aspect, the present disclosure is directed to a method for treating growth hormone deficiency, the method comprising a step of administering an hGH fusion protein GX-H9 to a pediatric patient with growth hormone deficiency once every two weeks at a dose of 0.8 to 3.2 mg per body weight kg of the patient.

As used herein, the term "hGH fusion protein GX-H9" refers to a human growth hormone fusion protein hGH-hyFc produced by fusing a hybrid Fc to a human growth hormone (hGH). The hGH fusion protein GX-H9 may comprise an amino acid sequence of SEQ ID NO: 1 attached herewith. The hGH fusion protein GX-H9 can be produced according to the method disclosed in U.S. Pat. No. 8,529,899 of which content is incorporated herein by reference in its entirety.

The pharmaceutical composition including the hGH fusion protein GX-H9 according to the present disclosure can be administered to pediatric patient with growth hormone deficiency.

"Short stature" means a case in which height is below 2 standard deviations (SD) or $3^{rd}$ percentile (3%) of normal or a case in which height grows by 5 cm or less per year. Growth hormone deficiency may include innate or acquired deficiency. Regarding innate deficiency, when the pituitary gland does not develop so that growth hormone secretion disorder occurs, growth hormone deficiency may occur. Acquired growth hormone deficiency may occur due to damage to brain tissue caused by oxygen deficiency resulting from difficult delivery. Other causes of growth hormone deficiency include damage to the pituitary gland caused by radiation for treatment of a brain tumor or tuberculous meningitis after birth. Growth hormone deficiency shows symptoms such as growth retardation and short stature, and innate growth hormone deficiency shows low glucose symptoms, starting with the neonate. In addition, the child shows symptoms such as increased anxiety and reduced vitality.

The pharmaceutical composition of the present disclosure comprises a pharmaceutically acceptable carrier. The pharmaceutically acceptable carrier may be any carrier, as long as it is a non-toxic substance suitable for delivering the hGH fusion protein to the patient. Examples of the carrier that can be used in the present disclosure include sterile water, alcohols, fats, waxes, and inert solids. Pharmaceutically acceptable adjuvants such as buffering agents, dispersing agents, diluents, and the like, i.e., bacteriostatic water for injection (BWFI), phosphate-buffered saline, Ringer's solution, dextrose solution, sucrose solution, poloxamer solution, and the like may also be incorporated in the pharmaceutical compositions of the present disclosure.

In the present disclosure, the hGH fusion protein GX-H9 may be administered once a week at a dose of 0.4 to 1.6 mg per body weight kg of a pediatric patient, for example, once a week at a dose of 0.6, 0.7, 0.8, 0.9, 1.0, 1.1 or 1.2 mg per body weight kg of the patient. Preferably, the hGH fusion protein GX-H9 may be administered once a week at a dose of 0.5 to 1.5 mg, 0.7 to 1.3 mg, or 0.8 to 1.2 mg per body weight kg of the patient. In addition, the hGH fusion protein GX-H9 may be administered once every two weeks at a dose of 0.8 to 3.2 mg per body weight kg of a pediatric patient, for example, once every two weeks at a dose of 1.0, 1.2, 1.4, 1.6, 1.8, 2.0, 2.2, 2.4, 2.6 or 2.8 mg per body weight kg of the patient. Preferably, the hGH fusion protein GX-H9 may be administered once every two weeks at a dose of 1.0 to 3.0 mg, 1.4 to 2.6 mg, or 1.6 to 2.4 mg per body weight kg of the patient. More Preferably, the hGH fusion protein GX-H9 is administered once a week at a dose of 0.8 to 1.2 mg per body weight kg of the patient, or once every two weeks at a dose of 1.6 to 2.4 mg per body weight kg of the patient.

The dose of the hGH fusion protein can be regulated based on the body weight of the patient, and can be increased or decreased depending on the progress after administration. The dose of hGH fusion protein that is subsequently administered may be higher or lower than the initial dose or may be equal to the initial dose. In an initial stage, the hGH fusion protein may be administered at a low dose in order to ensure safety, and when it is confirmed that adverse events or the like do not appear, the dose may be increased gradually. In addition, the dose of the hGH fusion protein may be regulated while monitoring the IGF-I SDS value in a plasma or serum sample obtained from the patient. The dose of hGH fusion protein suitable for an individual patient may vary depending on the age, sex, constitution, body weight and the like of the patient.

The pharmaceutical composition containing the hGH fusion protein GX-H9 may be administered to a subject in various ways. For example, the pharmaceutical composition may be administered parenterally, for example, subcutaneously or intravenously. This composition may be sterilized using a conventional sterilization technique well known in the art. The composition may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the hGH fusion protein in these formulations can vary widely, and may be selected primarily based on fluid volumes, viscosities, etc., in accordance with the particular mode of administration selected.

In still another aspect, the present disclosure is directed to a kit comprising: a container containing an hGH fusion protein GX-H9 and a pharmaceutically acceptable carrier; and an insert indicating that the hGH fusion protein is administered to a pediatric patient once a week at a dose of 0.4 to 1.6 mg/kg per body weight kg of the patient in order to treat growth hormone deficiency. In particular, the present disclosure is directed to a kit comprising: a container containing an hGH fusion protein GX-H9 and a pharmaceutically acceptable carrier; and an insert indicating that the hGH fusion protein is administered to a pediatric patient once every two weeks at a dose of 0.8 to 3.2 mg/kg per body weight kg of the patient in order to treat growth hormone deficiency.

The insert may be a type of guide indicating that the hGH fusion protein is administered to a pediatric patient in order to treat growth hormone deficiency.

The hGH fusion protein and the pharmaceutically acceptable carrier may be present in the same container or individual containers. In one embodiment, suitable containers may include bottles, vials, bags, syringes (e.g., a dose-controllable pen type, a syringe enabling immediate administration by mixing a solvent and a freeze-dried agent after removal of a barrier, etc.), and the like. The container may be formed of various materials, for example, glass, a plastic material or a metal. A label included in the container may indicate use instructions. Additionally, from a commercial viewpoint and a user viewpoint, the kit may include other preferable materials, for example, a buffer, a diluent, a filter, a needle, a syringe, etc.

EXAMPLES

Hereinafter, the present disclosure will be described in further detail with reference to examples. It will be obvious to a person having ordinary skill in the art that these examples are illustrative purposes only and are not to be construed to limit the scope of the present disclosure.

Example 1: Production of hGH Fusion Protein GX-H9

The hGH fusion protein GX-H9 can be produced according to the method disclosed in U.S. Pat. No. 8,529,899.

First, the nucleic acid sequence of hGH-hyFc, wherein hyFc is fused to a human growth hormone (hGH) encoding the amino acid sequence of SEQ ID NO: 1, was inserted into the expression vector pAD15, thereby constructing a cell line expressing and producing hGH-hyFc. To construct a vector comprising an hGH-hyFc structural gene, as the human growth hormone (hGH) gene, a sequence of GenBank AAA98618.1 was used, and as the hyFc gene, sequences of GenBank P01880 (IgD) and GenBank AAH25985 (IgG4) were used for fusion. The genes obtained from gene producers were inserted into an expression vector for production of a fusion protein-producing cell line, by use of specific restriction enzymes.

The expression vector obtained by the above-described method was transfected into CHO DG44 (Columbia University, USA) cells by a calcium phosphate method. At 6 hours after transfection, the transfected cells were washed with phosphate buffer, and then the medium was replaced with 10% dFBS (Gibco, USA, 30067-334), MEM alpha (Gibco, 12561, USA, Cat No. 12561-049), HT+(Gibco, USA, 11067-030)) medium. At 48 hours after transfection, the cells were serially diluted with HT-free 10% dFBS+ MEM alpha medium on a 100 mm plate, and HT selection was performed. The cells were allowed to stand until single colonies were formed, while the medium was replaced twice a week. Next, to increase productivity using a DHFR-system, MTX amplification of the HT-selected clones was performed. After completion of MTX amplification, the cells were subcultured about 4-5 times for stabilization, and then evaluation of unit productivity was performed, thereby obtaining clones suitable for production of the desired protein.

To obtain a single clone for the clone showing the highest productivity, limiting dilution cloning (LDC) was performed. For LDC, the cells were diluted with medium and seeded into a 96-well plate at a concentration of 1 cell/well. On 10 to 14 days after seeding, cells were collected from wells containing single clones under microscopic observation, and the collected cells were cultured in a T25 flask so that productivity evaluation for the cells could be performed. Then, a cell line having high productivity was selected.

The culture medium was collected from the selected cell line, and then the desired protein was purified from the culture medium. To this end, the protein-containing culture medium sample was adsorbed (sample binding) using Prosep Ultra Plus (Prosep® Ultra Plus, Merck), and then equilibrated using 50 mM sodium phosphate, 150 mM sodium chloride and pH 7.0 buffer. An XK16/20 column (GE Healthcare) was used for elution, and the desired protein was eluted using 100 mM sodium citrate, 200 mM L-arginine and pH 3.1 buffer.

Example 2: Test for Antibody-Dependent Cellular Cytotoxicity (ADCC) and Complement-Dependent Cytotoxicity (CDC) of hGH Fusion Protein GX-H9

In order to confirm that the hybrid Fc region of GX-H9 does not induce antibody dependent cell mediated cytotoxicity (ADCC) and complement dependent cytotoxicity (CDC), enzyme-linked immunosorbent assay (ELISA) was performed.

As positive controls, Rituxan (Roche, Switzerland) and Enbrel (Amgen, USA), known to have a very high binding affinity for Fcγ receptor (FcγR) I, II and III, were used. Each of GX-H9, Rituxan and Enbrel was coated on a 96-well plate, and then allowed to react with serially diluted Fcγ receptor I. After completion of the reaction, each of the reaction solutions was washed with buffer to remove Fcγ receptor I not bound to the test substances. Next, the binding affinity between Fcγ receptor I and each of the test substances was measured using biotinylated anti-FcγRI antibody and HRP-conjugated streptavidin.

The binding affinity between GX-H9 and C1q that induces complement-dependent cytotoxicity was also measured using the ELISA method as described above. As positive controls, Rituxan (Roche, Switzerland) and Enbrel (Amgen, USA) were used, and the binding affinity between C1q and each of the test substances was measured using HRP-conjugated anti-C1q antibody.

Figure 2:
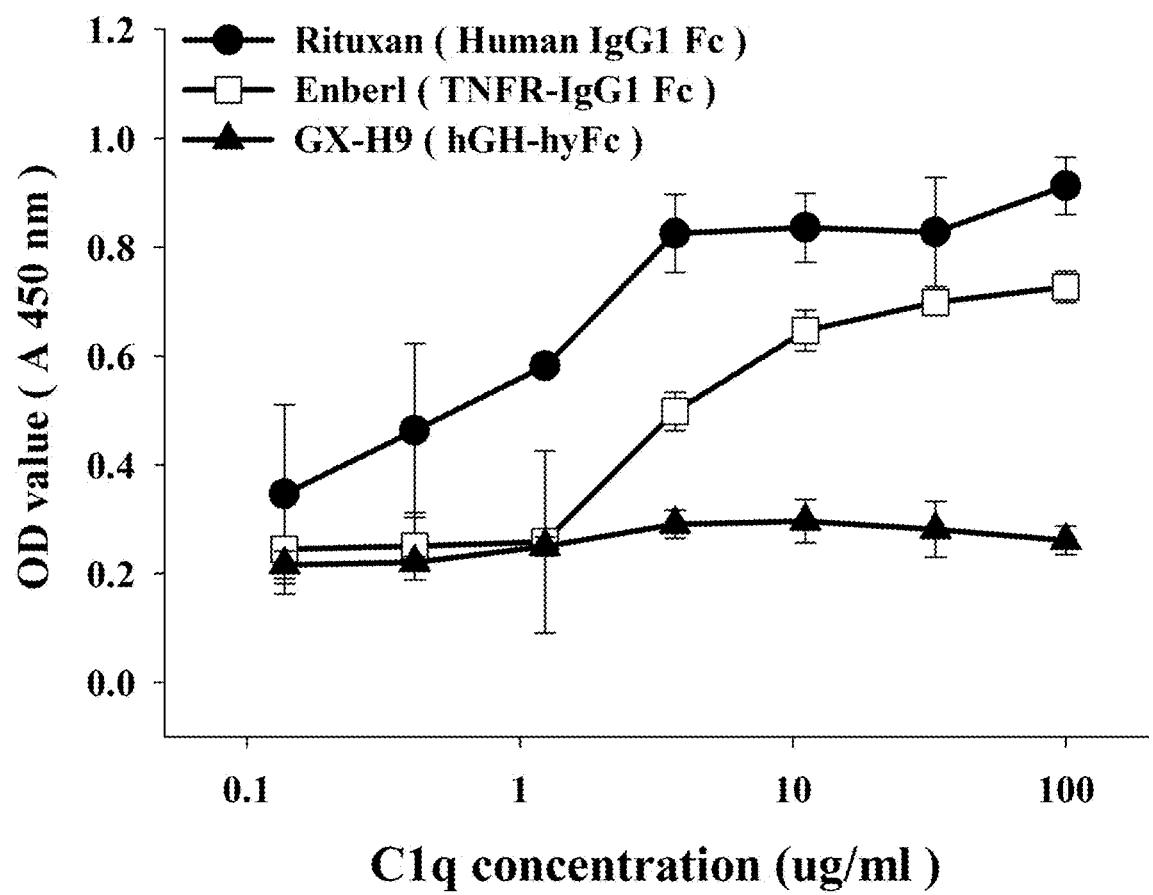
FIG. 2 shows the result of measuring the binding affinity of C1q for an hGH fusion protein (GX-H9).

As a result, as shown in FIG. 1, GX-H9 showed low binding affinity for Fcγ receptor I that induces antibody-dependent cellular cytotoxicity, and as can be seen in FIG. 2, GX-H9 also had low binding affinity for C1q that induces complement-dependent cytotoxicity.

Example 3: Results of Preclinical Trial for hGH Fusion Protein (GX-H9)

3-1: Test for Effect of Repeated Subcutaneous Administration of GX-H9 Using Hypophysectomized Rats The effect of GX-H9 was tested using hypophysectomized rats that are animal disease models. As a control, Genotropin (Pfizer, USA) that is a once-daily dose form was used. GX-H9 was administered once a week, and the effect thereof was compared with that of the control.

A test was performed on individuals showing a body weight gain of about 10% or less during about one week after hypophysectomization. Group 1 as a negative control was administered subcutaneously with a vehicle alone for 2 weeks. Group 2 was administered with Genotropin everyday at a dose of 0.2 mg/kg. Group 3 was administered subcutaneously with Genotropin once a week at a dose of 1.4 mg/kg, which is a weekly dose of Genotropin. Group 4 was administered subcutaneously with GX-H9 once a week at a dose of 1.4 mg/kg (corresponding to the weekly dose of Genotropin). Group 5 was administered subcutaneously with GX-H9 once a week at a dose of 3.5 mg/kg (corresponding to ½ to molar number of the weekly dose of Genotropin). Group 6 was administered subcutaneously with GX-H9 once a week at a dose of 7.0 mg/kg (corresponding to the identical molar number to that of the weekly dose of Genotropin). Each day after drug administration, symptoms in each rat were observed, and the weight of each rat was measured.

Figure 3:
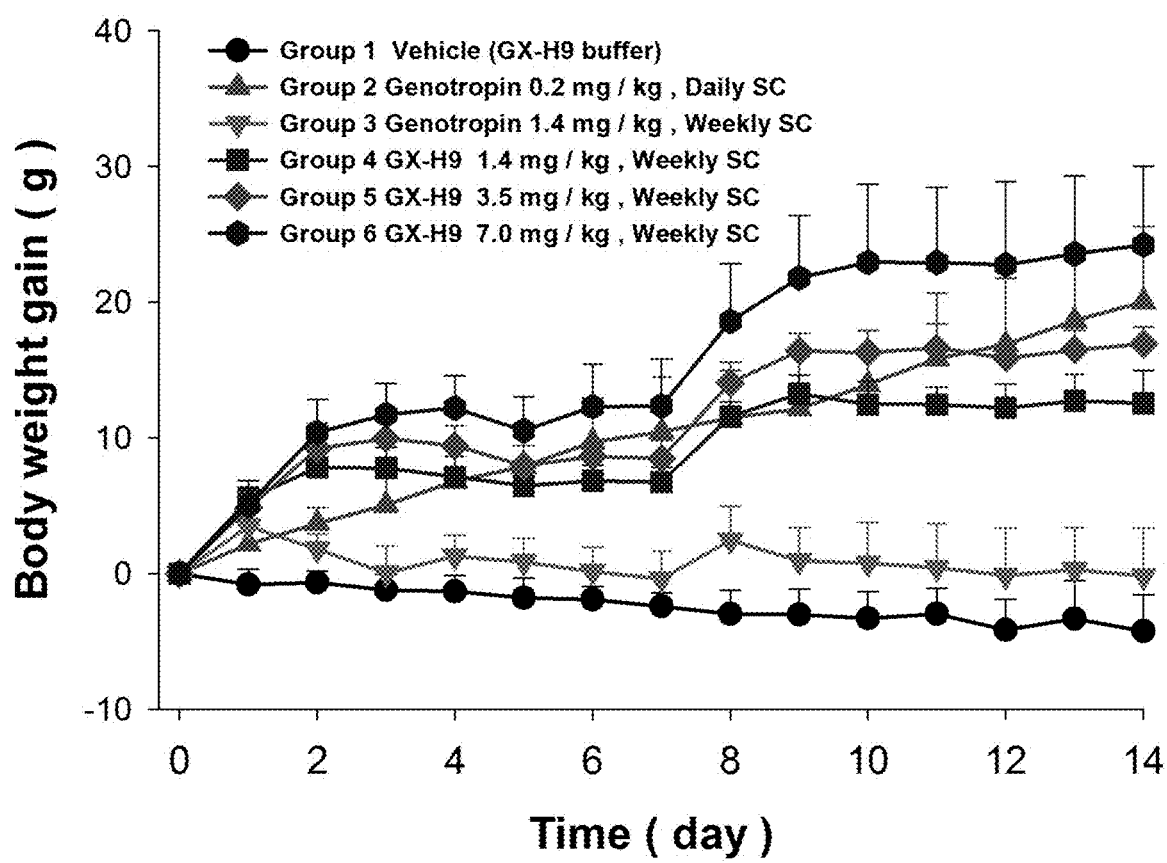
FIG. 3 shows the results of measuring body weight gains in hypophysectomized rats after administration of Genotropin (Pfizer) or GX-H9.

As a result, as shown in FIG. 3, when Genotropin was administered once a day at a dose of 0.2 mg/kg, a mean body weight of about 20 g was gained, but when Genotropin was administered once a week at a dose of 1.4 mg/kg, there was no gain of body weight. When GX-H9 was administered once a week at a dose of 7 mg/kg (group 6), group 6 showed a higher body weight gain compared to group 3 administered with Genotropin at the identical molar number. In addition, administration of 3.5 mg/kg of GX-H9 (group 5) showed a similar effect to that of daily administration of 0.2 mg/kg of Genotropin (group 2).

3-2: Pharmacokinetic Study after Single Dose Subcutaneous Administration of hGH Fusion Protein (GX-H9) Using Rats To test the pharmacokinetics of GX-H9, rats were administered subcutaneously with single dose GX-H9. As a control, single dose Eutropin (LG Life Sciences, Ltd., Korea) was administered to rats for comparison of the effects. Group 1 was administered subcutaneously with single dose 200 μg/kg of Eutropin, and group 2 was administered subcutaneously with single dose 200 μg/kg of GX-H9. Group 3 was administered subcutaneously with single dose 1,000 μg/kg of GX-H9.

Before subcutaneous administration and at 1, 4, 8, 12, 18, 24, 36, 48, 72, 96, 120, 144, 168, 216, 264 and 336 hours after subcutaneous administration, blood was sampled from the rats. The blood concentration of each test substance was measured using a biosample analysis method (ELISA) specific for each test substance.

Figure 4:
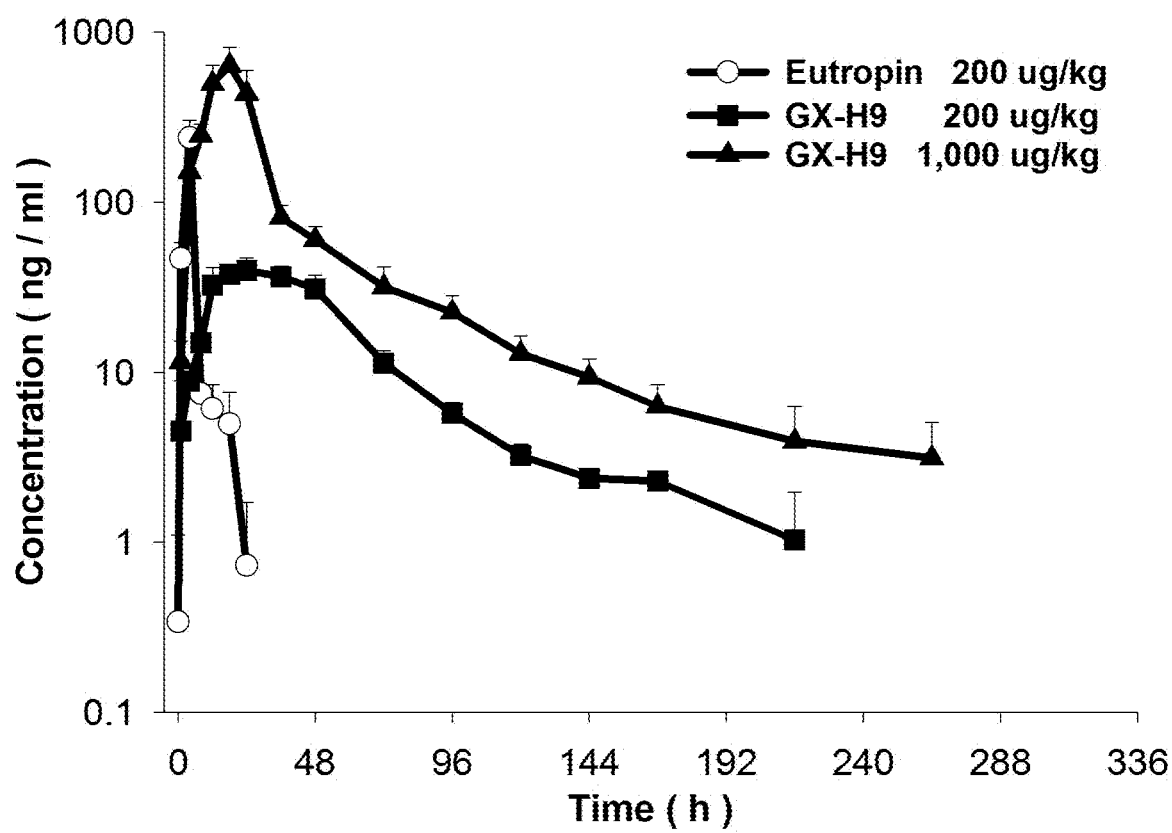
FIG. 4 shows the pharmacokinetic characteristics of an hGH fusion protein (GX-H9) or Eutropin (LG Life Sciences), shown after single dose subcutaneous administration of each of the drugs to rats.

The test results are shown in FIG. 4 and Table 1 below. As can be seen therein, in pharmacokinetics after single dose GX-H9 was administered subcutaneously at a dose of 200 or 1,000 μg/kg, the peak blood concentration was reached at 17 hours or 24 hours ($T_{max}$), and GX-H9 was detected in the blood up to 9 days and 11 days, respectively. As the dose of administration was increased, systemic exposure was also increased.

TABLE 1

| PK parameters | Eutropin 200 μg/kg | GX-H9 200 μg/kg | GX-H9 1,000 μg/kg |
|---|---|---|---|
| Rsq | 0.88 ± 0.08 | 0.93 ± 0.04 | 0.99 ± 0.01 |
| $T_{max}$ (h) | 4.00 ± 0.00 | 24.0 ± 8.49 | 16.8 ± 2.68 |
| $C_{max}$ (ng/mL) | 240 ± 64 | 42 ± 4 | 650 ± 158 |
| Lambda_z | 3.00 ± 0.00 | 6.80 ± 2.17 | 7.60 ± 0.89 |
| Lambda_z lower | 10 ± 2 | 46 ± 25 | 38 ± 5 |
| Lambda_z upper | 20 ± 3 | 182 ± 32 | 206 ± 40 |
| $AUC_{last}$ (ng · h/mL) | 1,019 ± 246 | 2,477 ± 303 | 16,165 ± 2,961 |
| $T_{1/2}$ (h) | 5.6 ± 1.0 | 35.7 ± 5.0 | 37.1 ± 4.1 |

When compared with the group administered with 200 μg/kg of Eutropin, which is the control substance, in case of the group administered subcutaneously with 200 μg/kg of GX-H9, the test substance was detected in the blood for a longer period of time (24 hours for Eutropin vs. 9 days for GX-H9), and GX-H9 was maintained in the blood, while the time ($T_{max}$) taken to reach the maximum blood concentration showed a difference of about 20 hours (4 hours for Eutropin vs. 24 hours for GX-H9). Such results indicate that the rats were systematically exposed to GX-H9 for a longer period of time compared to the control drug Eutropin. In addition, as the dose of GX-H9 was increased, systemic exposure after subcutaneous administration is increased in proportion to an increase rate of the dose.

3-3: Pharmacokinetic Study after Subcutaneous Administration of hGH Fusion Protein (GX-H9) Using Monkeys The pharmacokinetics of GX-H9 and the control substance Eutropin in cynomolgus monkeys were analyzed. GX-H9 was administered subcutaneously once a week repeating with a total of four times at doses of 500 μg/kg and 1,000 μg/kg, and the control substance Eutropin was administered subcutaneously at a single dose of 1,000 μg/kg to male monkeys (3 monkeys per group).

In the groups administered with GX-H9, blood was sampled before the first and fifth administrations (day 0 and day 21) and at 1, 4, 8, 12, 18, 24, 30, 36, 48, 60, 72, 96, 120, 144 and 168 hours after administration.

In the groups administered with Eutropin, blood was sampled before single dose administration and at 1, 4, 8, 12, 18, 24, 30, 36, 48, 60, 72, 96, 120, 144 and 168 hours after single dose administration.

Figure 5:
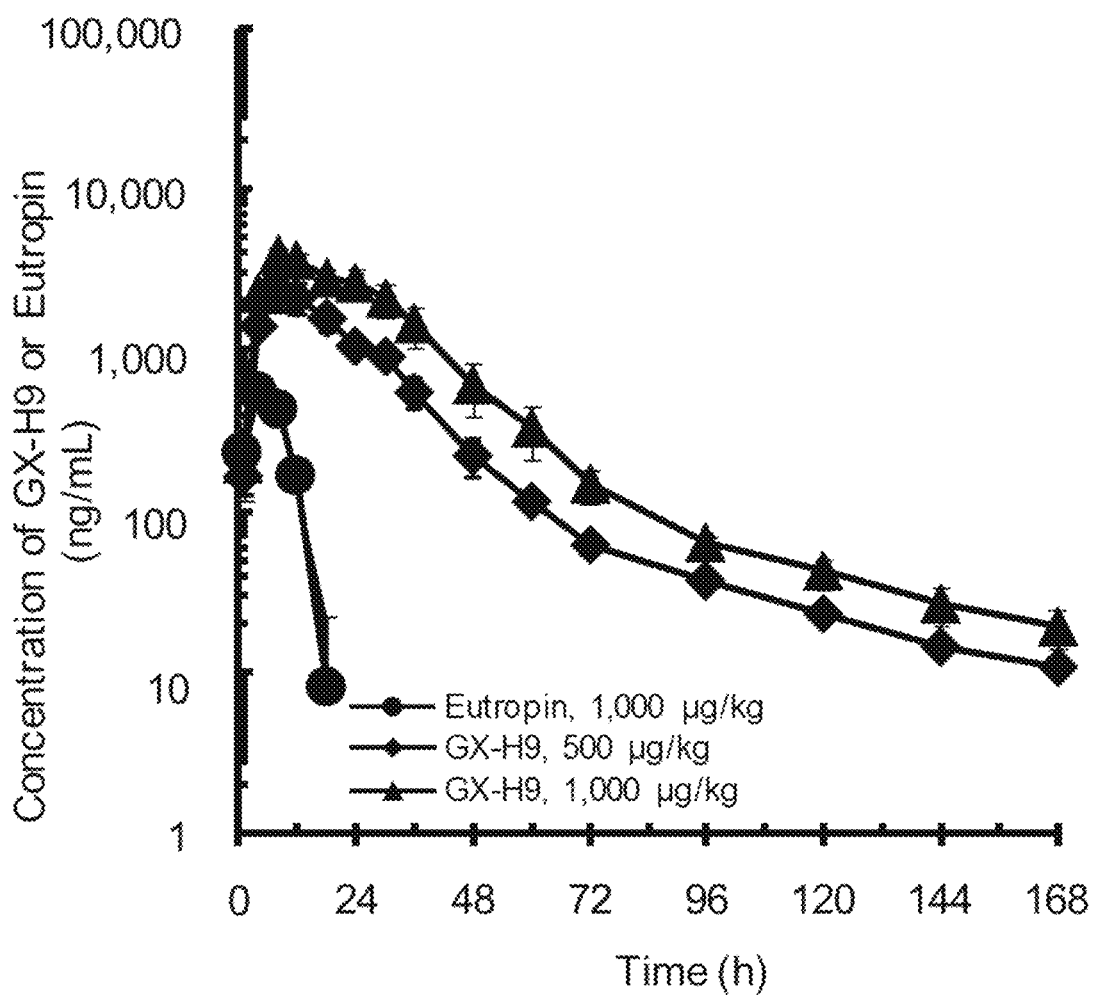
FIG. 5 shows the pharmacokinetic characteristics of an hGH fusion protein (GX-H9) or Eutropin, shown after single dose subcutaneous administration of each of the drugs to monkeys.
Figure 6:
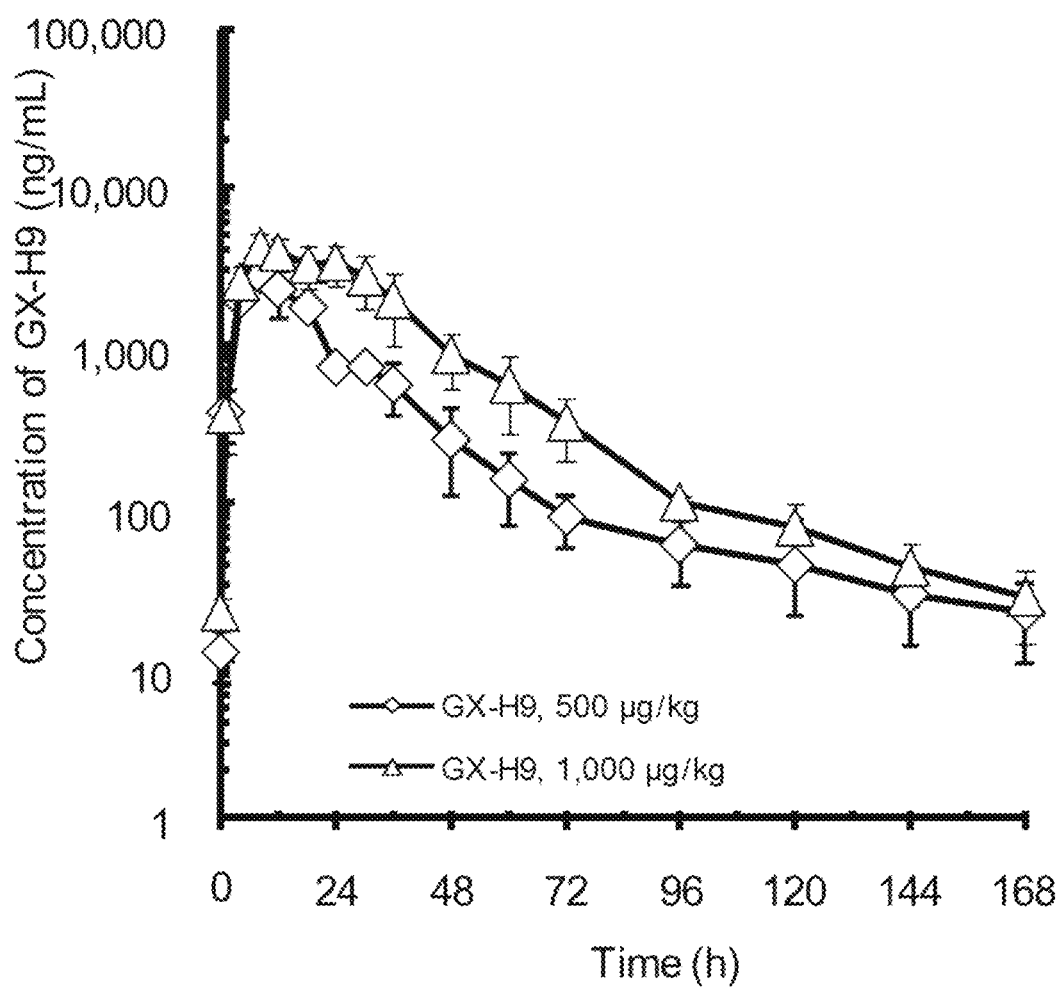
FIG. 6 shows the pharmacokinetic characteristics of an hGH fusion protein (GX-H9), shown after GX-H9 was administered repeatedly to monkeys for 4 weeks.

The blood concentrations of the test substances were measured using a biosample analysis method (ELISA) specific for each of GX-H9 and Eutropin, and the results are shown in FIG. 5 and Table 2 below (single dose administration) and FIG. 6 and Table 3 below (repeated administration). As can be seen from FIGS. 5, 6, Tables 2 and 3, when GX-H9 was administered at a dose of 500 or 1,000 μg/kg, systemic exposure increased according to an increase in the dose after both single administration and repeated administration (4 weeks).

TABLE 2

| Article | | $T_{1/2,z}$ (h) | $T_{max}$ (h) | $C_{max}$ (ng/mL) | $AUC_{last}$ (ng · h/mL) | $AUC_{inf}$ (ng · h/mL) | Vz/F (mL/kg) | CL/F (mL/h/kg) | $MRT_{last}$ (h) | $MRT_{inf}$ (h) |
|---|---|---|---|---|---|---|---|---|---|---|
| Eutropin (1,000 μg/kg) | Mean | 3.7 | 5.3 | 551 | 4457 | 5207 | 997 | 192.55 | 6.2 | 8.0 |
| | SD | 1.2 | 2.3 | 66 | 282 | 318 | 285 | 12.02 | 0.7 | 0.7 |
| | CV (%) | 33.0 | 43.3 | 12.0 | 6.3 | 6.1 | 29 | 6.2 | 10.7 | 8.7 |
| GX-H9 (500 μg/kg) | Mean | 37.9 | 8.0 | 2370 | 57732 | 58270 | 479 | 8.70 | 24.1 | 26.0 |
| | SD | 3.6 | 0.0 | 562 | 8722 | 8685 | 101 | 1.26 | 0.6 | 0.8 |
| | CV (%) | 9.5 | 0.0 | 23.7 | 15.1 | 14.9 | 21.1 | 14.5 | 2.4 | 2.9 |
| GX-H9 (1,000 μg/kg) | Mean | 41.9 | 8.0 | 3878 | 115668 | 116825 | 534 | 8.73 | 26.2 | 28.4 |
| | SD | 7.5 | 0.0 | 463 | 19735 | 19622 | 158 | 1.56 | 1.4 | 1.9 |
| | CV (%) | 17.9 | 0.0 | 11.9 | 17.1 | 16.8 | 30 | 17.9 | 5.3 | 6.8 |

TABLE 3

| Article | | $T_{1/2,z}$ (h) | $T_{max}$ (h) | $C_{max}$ (ng/mL) | $AUC_{last}$ (ng · h/mL) | $AUC_{inf}$ (ng · h/mL) | Vz/F (mL/kg) | CL/F (mL/h/kg) | $MRT_{last}$ (h) | $MRT_{inf}$ (h) |
|---|---|---|---|---|---|---|---|---|---|---|
| GX-H9 (500 μg/kg) | Mean | 46.4 | 8.0 | 2738 | 61775 | 63143 | 539 | 8.18 | 25.0 | 29.3 |
| | SD | 5.3 | 0.0 | 391 | 12719 | 13581 | 60 | 1.85 | 2.9 | 5.0 |
| | CV (%) | 11.4 | 0.0 | 14.3 | 20.6 | 21.5 | 11 | 22.6 | 11.6 | 16.9 |
| GX-H9 (1,000 μg/kg) | Mean | 32.3 | 9.3 | 4394 | 144268 | 145466 | 339 | 7.14 | 29.4 | 31.1 |
| | SD | 4.5 | 2.3 | 926 | 35579 | 35071 | 116 | 1.69 | 2.0 | 1.9 |
| | CV (%) | 14.0 | 24.7 | 21.1 | 24.7 | 24.1 | 34 | 23.6 | 6.7 | 6.3 |

When compared to the control drug Eutropin (1,000 μg/kg, administered subcutaneously with single dose), in case of administration of GX-H9 (500 or 1,000 μg/kg), the test substance was detected in the blood for a longer period (12 to 18 hours after administration of Eutropin vs. 168 hours after administration of GX-H9). Namely, when GX-H9 was administered subcutaneously, the monkeys were systematically exposed to GX-H9 for a longer period of time compared to the control drug Eutropin. In addition, it was shown that, as the dose of GX-H9 increased from 500 to 1,000 μg/kg, systemic exposure after subcutaneous administration of GX-H9 is increased in proportion to an increase rate of the dose.

Example 4: Results of Phase-1 Clinical Trial for hGH Fusion Protein (GX-H9)

4-1: Pharmacokinetic Characteristics of hGH Fusion Protein (GX-H9) in Healthy Adults On healthy volunteers, a phase-1 clinical trial was performed using random allocation, double blind, placebo control, single dose administration, and a stepwise increase in dose. The phase-1 clinical trial aimed to evaluate the safety, drug resistance and pharmacokinetic/pharmacodynamic characteristics upon single dose administration of GX-H9. Healthy volunteers were allocated randomly into test groups or placebo groups, and then administered subcutaneously in a single dose with four doses (0.2, 0.4, 0.8 and 1.6 mg/kg) of GX-H9, and then evaluated for a total of 56 days.

In the groups administered with GX-H9, blood was sampled before single dose administration and at 0.25, 1, 2, 4, 6, 8, 12, 16, 24, 28, 32, 36, 40, 48, 54, 60, 72, 80, 96, 144, 312, 480, 648 and 1320 hours after single dose administration.

Figure 7:
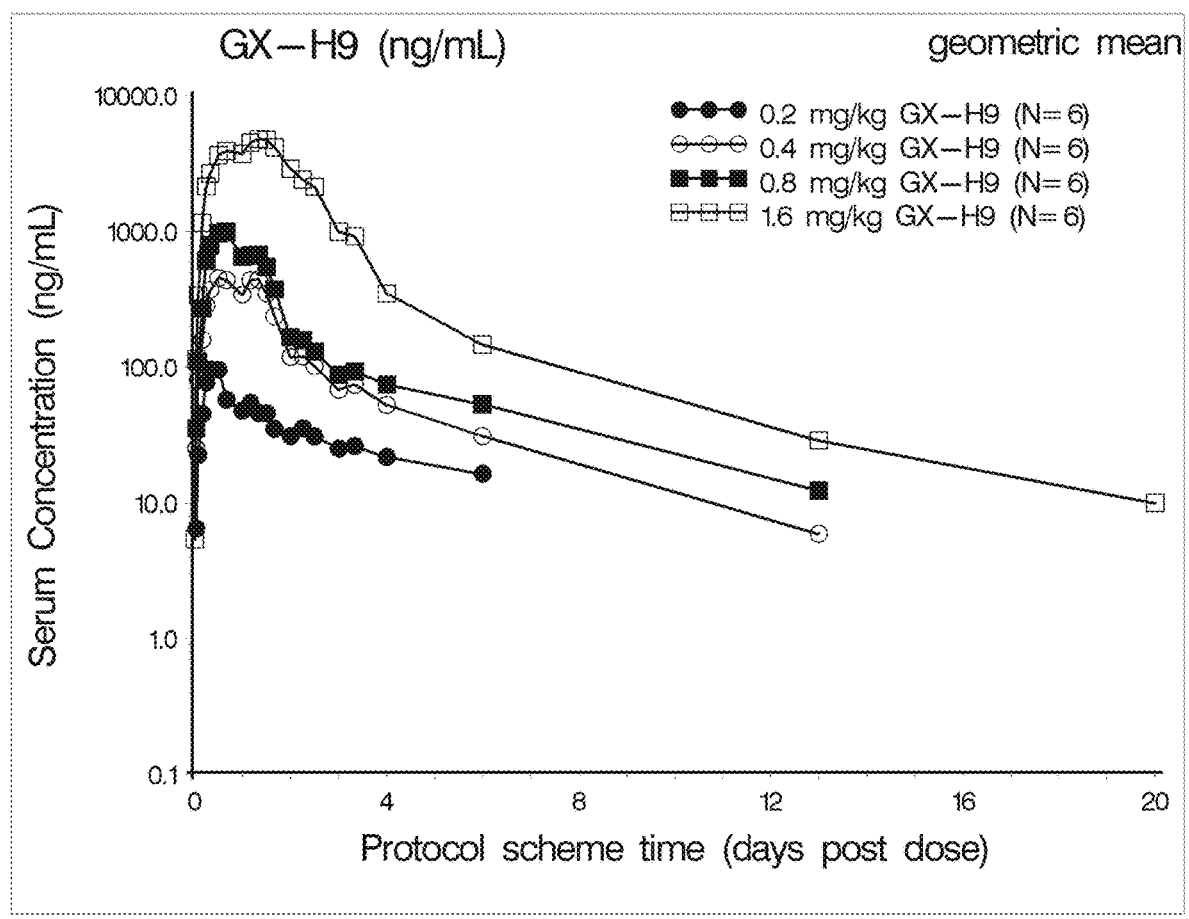
FIG. 7 shows the pharmacokinetic characteristics depending on the dose of an hGH fusion protein (GX-H9) in a phase-1 clinical trial on healthy adult volunteers.

The blood concentrations of GX-H9 were analyzed using a biosample analysis method (ELISA) specific for GX-H9, and the results are shown in Table 4 below and FIG. 7 [Mean (range)].

After single dose subcutaneous administration of GX-H9, the peak of geometric mean concentration was observed at about 12 hours (8 to 16 hours), and the second peak lower than the peak observed at about 12 hours was observed at about 32 hours (28 to 32 hours) after administration. The time taken to reach the maximum blood concentration was 12 to 16 hours in the 0.2-0.8 mg/kg dose group, and 34 hours in the 1.6 mg/kg dose group. The second peak in the highest dose group corresponded to $C_{max}$ (see FIG. 7). $C_{max}$ and AUC increased over doses across all doses. The half-life ($t_{1/2}$) was 69.2 hours to 138 hours and was different between individuals.

4-2: Pharmacokinetic Characteristics of hGH Fusion Protein (GX-H9) in Healthy Adults In the groups administered with GX-H9, blood was sampled before single dose administration and at 12, 24, 36, 48, 60, 72, 96, 144, 312, 480, 648 and 1320 hours after single dose administration. The results of percent changes from the baseline on the IGF-1 concentration in the sampled blood measured before administration are shown in FIG. 8.

Figure 8:
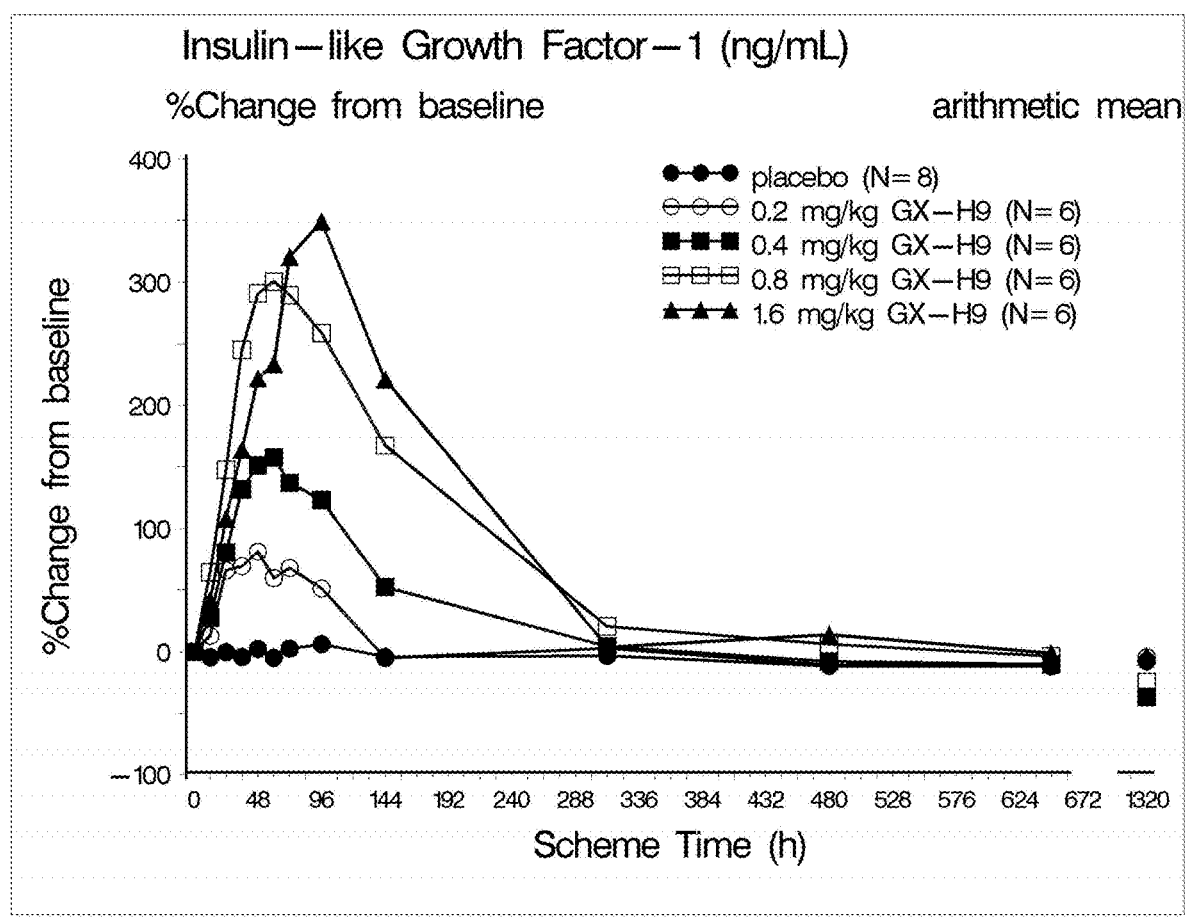
FIG. 8 shows the pharmacodynamic characteristics (IGF-1 SDS) depending on the dose of an hGH fusion protein (GX-H9) (changes from a baseline) in a phase-1 clinical trial on healthy adult volunteers.

FIG. 8 shows the percent changes (%) of blood IGF-1 concentration (ng/mL) from the baseline in the placebo group and the groups administered with 0.2, 0.4, 0.8 and 1.6 mg/kg of GX-H9. As can be seen therein, when GX-H9 was administered subcutaneously with a single dose at doses of 0.2, 0.4, 0.8 and 1.6 mg/kg, the blood IGF-1 concentration increased in a dose-dependent manner. The mean maximum increases (percent changes from the baseline) were 81%, 157%, 301% and 349% at doses of 0.2, 0.4, 0.8 and 1.6 mg/kg, respectively. The time taken for IGF-1 to reach the maximum blood concentration was 48 to 60 hours in the 0.2-0.8 mg/kg dose group, and 48 to 96 hours in the 1.6 mg/kg dose group, indicating that it increased in a dose-dependent manner. The mean concentration of IGF-1 was restored to the baseline on day 7 after administration at a dose of 0.2 mg/kg and on day 14 at other doses.

4-3: Examination of Safety of hGH Fusion Protein (GX-H9) in Healthy Adults

Treatment emergent adverse events observed in test subjects were analyzed according to an administered drug, the relation of adverse events with the drug, and the intensity of adverse events. The results are summarized in Table 5 below.

TABLE 4

| Group | $C_{max}$ (ng/mL) | $t_{max}$[1] (h) | $AUC_{0-t}$ (h · ng/mL) | $AUC_{0-inf}$ (h · ng/mL) | $t_{1/2}$ (h) | CL/F (L/h) | $V_z$/F (L) |
|---|---|---|---|---|---|---|---|
| 0.2 mg/kg GX-H9 (N = 6) | 105 (48.7-354) | 12.00 (8.00-28.00) | 6267 (3700-13952) | 8175 (5276-15544) | 112 (53.8-200) | 1.93 (1.07-2.69) | 312 (82.8-739) |
| 0.4 mg/kg GX-H9 (N = 6) | 571 (108-1240) | 14.01 (8.02-36.00) | 26339 (9711-50387) | 27350 (10371-51393) | 69.2 (37.8-86.4) | 1.09 (0.514-2.77) | 109 (54.1-304) |
| 0.8 mg/kg GX-H9 (N = 6) | 1095 (364-2300) | 16.00 (8.00-28.00) | 45361 (15432-109352) | 47286 (16864-117144) | 138 (79.4-1008) | 1.36 (0.535-4.36) | 271 (137-778) |
| 1.6 mg/kg GX-H9 (N = 6) | 5100 (2180-6790) | 34.00 (16.00-36.05) | 274161 (115210-396879) | 327672[2] (253881-398045) | 95.7[2] (71.3-143) | 0.361[2] (0.285-0.563) | 49.9[2] (32.9-58.7) |

[1] $t_{max}$ was presented as median value (range);
[2] n = 5 ($t_{1/2}$ value and parameters for one person could not be accurately determined).

TABLE 5

| | Severe | | | | | | Moderate | | | | | | Sum | | | | | | | | |
| --- | --- | --- | --- | --- | --- | --- | --- | --- | --- | --- | --- | --- | --- | --- | --- | --- | --- | --- | --- | --- | --- |
| | Related | | | Not Related | | | Related | | | Not Related | | | Related | | | Not Related | | | Sum | | |
| Group | E | n | (%) | E | n | (%) | E | n | (%) | E | n | (%) | E | n | (%) | E | n | (%) | E | n | (%) |
| Placebo control (N = 8) | 3 | 3 | (38%) | 6 | 4 | (50%) | | | | | | | 3 | 3 | (38%) | 6 | 4 | (50%) | 9 | 4 | (50%) |
| 0.2 mg/kg GX-H9 (N = 6) | 2 | 1 | (17%) | 5 | 3 | (50%) | | | | | | | 2 | 1 | (17%) | 5 | 3 | (50%) | 7 | 3 | (50%) |
| 0.4 mg/kg GX-H9 (N = 6) | 1 | 1 | (17%) | 7 | 3 | (50%) | | | | | | | 1 | 1 | (17%) | 7 | 3 | (50%) | 8 | 4 | (67%) |
| 0.8 mg/kg GX-H9 (N = 6) | 6 | 4 | (67%) | 4 | 3 | (50%) | | | | | | | 6 | 4 | (67%) | 4 | 3 | (50%) | 10 | 5 | (83%) |
| 1.6 mg/kg GX-H9 (N = 6) | 12 | 5 | (83%) | 7 | 4 | (67%) | | | | 1 | 1 | (17%) | 12 | 5 | (83%) | 8 | 4 | (67%) | 20 | 5 | (83%) |
| Total Active (N = 24) | 21 | 11 | (46%) | 23 | 13 | (54%) | | | | 1 | 1 | (4%) | 21 | 11 | (46%) | 24 | 13 | (54%) | 45 | 17 | (71%) |
| Total (N = 32) | 24 | 14 | (44%) | 29 | 17 | (53%) | | | | 1 | 1 | (3%) | 24 | 14 | (44%) | 30 | 17 | (53%) | 54 | 21 | (66%) |

N = Number of persons exposed to drug;
n = Number of persons who showed adverse events;
E = Number of adverse events that appeared;
(%) = Percentage of patients who experienced adverse events resulting from treatment, (n/N) * 100;
Serious adverse events or mild adverse events were not recorded.

As shown in FIG. 5, 21 of the test subjects, a total of 54 adverse events were reported. Death or serious adverse events were not reported. A severe adverse event was reported in one test subject, but it was determined that this severe adverse event would not be attributable to the drug. All adverse events excluding the above-described adverse event were mild. The most frequently reported adverse events were musculoskeletal and connective tissue disorders (19 cases), systemic disorders and administration site abnormality (11 cases), and neural disorders (10 cases). Three or more reported adverse events were muscle pains (7 cases), catheterization site responses (6 cases), headache (5 cases), nasopharyngitis (5 cases), joint pain (4 cases), and limb pain (3 cases).

Meanwhile, in the test subjects administered once with GX-H9, the presence or absence of an anti-drug antibody (ADA) was observed before administration and day 28 and day 56 after administration. As a result, patients with the antibody formed by GX-H9 did not appear.

Example 5: Results of Phase-2 Trial for hGH Fusion Protein (GX-H9)

5-1: Pharmacokinetic Characteristics of hGH Fusion Protein (GX-H9) in Patients with Pediatric Growth Hormone Deficiency In a randomized, open-labeled, active controlled, dose-finding study, a phase-2 clinical trial on patients with pediatric growth hormone deficiency is in progress in order to evaluate the safety, drug resistance, effectiveness and pharmacokinetic/pharmacodynamic characteristics of GX-H9 upon administration once a week or once every two weeks. GX-H9 was administered once a week at a dose of 0.8 mg/kg, once a week at a dose of 1.2 mg/kg, and once every two weeks at a dose of 2.4 mg/kg for a total of 6 months, and then the effectiveness and safety of GX-H9 was evaluated for a total of 24 months of administration including extended 18 months. As a control drug, Genotropin was administered at a dose of 0.03 mg/kg daily for 12 months.

The period of the clinical trial on the pediatric patients consisted of a screening period, a single dose administration period (4 weeks), a multiple dose administration-dose range determination period (6 months), an extended administration period (6 months), an additionally extended administration period (12 months), and a safety followed-up observation period (1 month). During the single-administration period, blood sampling for PK/PD analysis was performed in the following manner:

GX-H9 Cohort (Cohort 1; 0.8 mg/kg, once a week, Cohort 2; 1.2 mg/kg, once a week, and Cohort 3; 2.4 mg/kg, twice a month), sampling timing: 0 (−1 hr), 16 (±2 hrs), 40 (±2 hrs), 64 (±4 hrs), 88 (±4 hrs), 112 (±6 hrs), 160 (±12 hrs), 336 (±48 hrs) and 672 (±48 hrs).

Genotropin® Cohort (Cohort 4): sampling timing: 0 (−1 hr), 16 (±2 hrs), 88 (±4 hrs), 160 (±12 hrs), 336 (±48 hrs) and 672 (±48 hrs).

During the multiple administration-dose determination period (6 months), the determined dose was continuously administered. After 3 months, PK/PD analysis was performed in a steady state. Blood sampling was performed in the following manner.

For test subjects allocated to administration of GX-H9 once a week, blood sampling was performed on day 85 (including both PK and PD): 0 (−1 hr), 16 (±2 hrs), 40 (±2 hrs), 64 (±4 hrs), 88 (±4 hrs), 112 (±6 hrs) and 160 (±12 hrs).

For test subjects allocated to administration of GX-H9 twice a month, blood sampling was performed on day 85 (including both PK and PD): 0 (−1 hr), 16 (±2 hrs), 40 (±2 hrs), 64 (±4 hrs), 88 (±4 hrs), 112 (±6 hrs), 160 (±12 hrs) and 336 (±48 hrs).

For test subjects allocated to administration of Genotropin® Cohort once a day, blood sampling was performed on day 85, before retiring but after drug administration (including both PK and PD): 0 (−1 hr), 6 (±2 hrs), 12 (±2 hrs), 18 (±2 hrs), 24 (±2 hrs).

Figure 9:
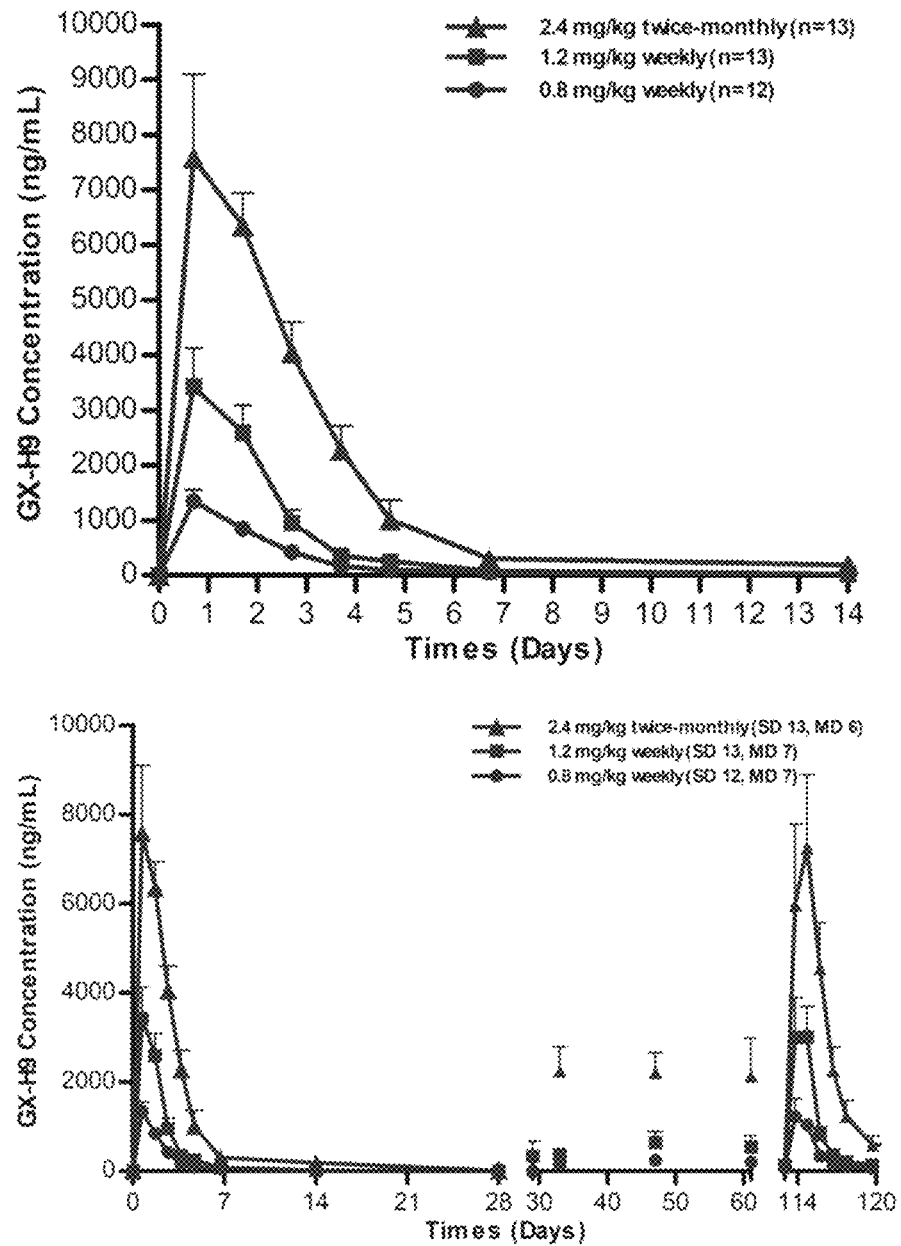
FIG. 9 shows the dose-dependent pharmacokinetic characteristics depending on the dose in single-dose (SD) period and multi-dose (MD) period of an hGH fusion protein (GX-H9) in a phase-2 clinical trial on patients with pediatric growth hormone deficiency.

As a result, as can be seen in FIG. 9, doses of 0.8, 1.2 and 2.4 mg/kg were all maintained in vivo at suitable levels without being accumulated in vivo.

5-2: Pharmacodynamic Characteristics of hGH Fusion Protein (GX-H9) in Patients with Pediatric Growth Hormone Deficiency Analysis of pharmacodynamic characteristics of the fusion protein was performed at the same timing as the blood sampling timing for pharmacodynamic analysis as described in Example 5-1 above.

During the single dose administration period, blood sampling for PK/PD analysis was performed in the following manner:

GX-H9 Cohort (Cohort 1, Cohort 2 and Cohort 3): sampling timing: 0 (−1 hr), 16 (±2 hrs), 40 (±2 hrs), 64 (±4 hrs), (±4 hrs), 112 (±6 hrs), 160 (±12 hrs), 336 (±48 hrs) and 672 (±48 hrs).

Genotropin® Cohort (Cohort 4): sampling timing: 0 (−1 hr), 16 (±2 hrs), 88 (±4 hrs), 160 (±12 hrs), 336 (±48 hrs) and 672 (±48 hrs).

During the multiple dose administration-dose range determination period, blood sampling was performed in the following manner:

PK/PD of test subjects allocated to administration of GX-H9 once a week: sampling timing: 0 (−1 hr), 16 (±2 hrs), (±2 hrs), 64 (±4 hrs), 88 (±4 hrs), 112 (±6 hrs) and 160 (±12 hrs).

PK/PD of test subjects allocated to administration of GX-H9 twice a month: sampling timing: 0 (−1 hr), 16 (±2 hrs), (±2 hrs), 64 (±4 hrs), 88 (±4 hrs), 112 (±6 hrs), 160 (±12 hrs), 336 (±48 hrs).

PK/PD of test subjects allocated to administration of Genotropin® Cohort once a day: sampling timing: 0 (−1 h), 6 (±2 hrs), 12 (±2 hrs), 18 (±2 hrs) and 24 (±2 hrs).

As a result, as can be seen in FIG. 10, all doses of 0.8, 1.2 and 2.4 mg/kg were maintained in vivo at suitable levels without being accumulated in vivo. Furthermore, it was confirmed that the mean IGF-1 SDS values in vivo were in the normal range (−2 SDS to 2 SDS).

5-3: Examination of Safety of hGH Fusion Protein (GX-H9) in Patients with Pediatric Growth Hormone Deficiency Adverse events observed in the test subjects were analyzed according to the administered drug and the relation of the drug with adverse events. As a result, it was shown that all the adverse events reported to date in the clinical trial on the pediatric patients were at the same levels as those observed in existing growth hormone treatment, indicating that GX-H9 is safe.

5-4: Examination of Anti-Drug Antibody (ADA) Against hGH Fusion Protein in Patients with Pediatric Growth Hormone Deficiency Immunogenicity was evaluated by determining whether an antibody would be formed by repeated administration of GX-H9. Until now, antibody formation by administration of GX-H9 was not observed on all the patients.

It is known that the dose of the conventional first-generation (daily dose) hGH recommended for treatment of patients with pediatric growth hormone deficiency is 0.16 mg/kg to 0.24 mg/kg per week. According to the present disclosure, it was found that the suitable dose of the hGH fusion protein for patients with pediatric growth hormone deficiency is 0.4 mg/kg to 1.6 mg/kg when it is administered once a week, and 0.8 mg/kg to 3.2 mg/kg when it is administered once every two weeks. In addition, single or multiple administration of the hGH fusion protein (GX-H9) to pediatric patients showed no serious adverse event.

Therefore, it was found that GX-H9 has efficacy equal to in vivo growth hormone or the first-generation growth hormone products and, at the same time, has an increased half-life, and thus shows a significantly improved patient compliance, and it is also safe.

INDUSTRIAL APPLICABILITY

According to the present disclosure, when the hGH fusion protein GX-H9 is administered to once a week at a dose of 0.4 to 1.6 mg per body weight kg of pediatric patients with growth hormone deficiency, or administered twice every two weeks at a dose of 0.8 to 3.2 mg per body weight kg of pediatric patients, the growth hormone can be long-lasting in vivo so that the IGF-1 SDS value thereof can be maintained in a normal range for a long period of time, and thus a growth hormone formulation can be administered once a week or once every two weeks without the necessity of administering daily, thereby treating growth hormone deficiency.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

The invention claimed is:

1. A method for treating growth hormone deficiency of a subject in need thereof, comprising the following step (i) or step (ii):
   (i) administering an hGH fusion protein GX-H9 to the subject once a week at a dose of 0.4 to 1.5 mg per body weight kg of the subject, or
   (ii) administering an hGH fusion protein GX-H9 to the subject once every two weeks at a dose of 0.8 to 3.0 mg per body weight kg of the subject,
   wherein the hGH fusion protein GX-H9 comprises the amino acid sequence of SEQ ID NO: 1; and
   wherein the subject is a pediatric patient.

2. The method of claim 1, wherein, in the step (i), the dose is 0.5 to 1.5 mg per body weight kg of the subject.

3. The method of claim 1, wherein, in the step (ii), the dose is 1.0 to 3.0 mg per body weight kg of the subject.

4. The method of claim 1, wherein in step (i) and step (ii), the hGH fusion protein GX-H9 is subcutaneously administered.

5. The method of claim 1, wherein, in the step (i), the dose is 0.8 to 1.2 mg per body weight kg of the subject.

6. The method of claim 1, wherein, in the step (ii), the dose is 1.6 to 2.4 mg per body weight kg of the subject.

7. The method of claim 1, which further comprises monitoring an insulin like growth factor-1 level standard deviation score (IGF-1 SDS) in a plasma or serum sample obtained from the subject, wherein the dose of the hGH fusion protein GX-H9 is adjusted within the range from 0.4 mg to 1.5 mg per body weight kg of the subject in step (i) and from 0.8 mg to 3.0 mg per body weight kg of the subject in step (ii), to maintain the IGF-1 SDS in a range from −2 to 2.

* * * * *

SEQUENCE LISTING

```
<160> NUMBER OF SEQ ID NOS: 1

<210> SEQ ID NO 1
<211> LENGTH: 436
<212> TYPE: PRT
<213> ORGANISM: Artificial Sequence
<220> FEATURE:
<223> OTHER INFORMATION: GX-H9

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
```

```
                65                  70                  75                  80
            Leu Leu Ile Gln Ser Trp Leu Glu Pro Val Gln Phe Leu Arg Ser Val
                            85                  90                  95

Phe Ala Asn Ser Leu Val Tyr Gly Ala Ser Asp Ser Asn Val Tyr Asp
                        100                 105                 110

Leu Leu Lys Asp Leu Glu Glu Gly Ile Gln Thr Leu Met Gly Arg Leu
                        115                 120                 125

Glu Asp Gly Ser Pro Arg Thr Gly Gln Ile Phe Lys Gln Thr Tyr Ser
                        130                 135                 140

Lys Phe Asp Thr Asn Ser His Asn Asp Asp Ala Leu Leu Lys Asn Tyr
            145                 150                 155                 160

Gly Leu Leu Tyr Cys Phe Arg Lys Asp Met Asp Lys Val Glu Thr Phe
                        165                 170                 175

Leu Arg Ile Val Gln Cys Arg Ser Val Glu Gly Ser Cys Gly Phe Arg
                        180                 185                 190

Asn Thr Gly Arg Gly Glu Glu Lys Lys Glu Lys Glu Lys Glu Lys Glu
                        195                 200                 205

Glu Gln Glu Glu Arg Glu Thr Lys Thr Pro Glu Cys Pro Ser His Thr
                        210                 215                 220

Gln Pro Leu Gly Val Phe Leu Phe Pro Pro Lys Pro Lys Asp Thr Leu
            225                 230                 235                 240

Met Ile Ser Arg Thr Pro Glu Val Thr Cys Val Val Asp Val Ser
                        245                 250                 255

Gln Glu Asp Pro Glu Val Gln Phe Asn Trp Tyr Val Asp Gly Val Glu
                        260                 265                 270

Val His Asn Ala Lys Thr Lys Pro Arg Glu Glu Gln Phe Asn Ser Thr
                        275                 280                 285

Tyr Arg Val Val Ser Val Leu Thr Val Leu His Gln Asp Trp Leu Asn
                        290                 295                 300

Gly Lys Glu Tyr Lys Cys Lys Val Ser Asn Lys Gly Leu Pro Ser Ser
            305                 310                 315                 320

Ile Glu Lys Thr Ile Ser Lys Ala Lys Gly Gln Pro Arg Glu Pro Gln
                        325                 330                 335

Val Tyr Thr Leu Pro Pro Ser Gln Glu Glu Met Thr Lys Asn Gln Val
                        340                 345                 350

Ser Leu Thr Cys Leu Val Lys Gly Phe Tyr Pro Ser Asp Ile Ala Val
                        355                 360                 365

Glu Trp Glu Ser Asn Gly Gln Pro Glu Asn Asn Tyr Lys Thr Thr Pro
                        370                 375                 380

Pro Val Leu Asp Ser Asp Gly Ser Phe Phe Leu Tyr Ser Arg Leu Thr
            385                 390                 395                 400

Val Asp Lys Ser Arg Trp Gln Glu Gly Asn Val Phe Ser Cys Ser Val
                        405                 410                 415

Met His Glu Ala Leu His Asn His Tyr Thr Gln Lys Ser Leu Ser Leu
                        420                 425                 430

Ser Leu Gly Lys
                        435
```